(12) United States Patent
Yang et al.

(10) Patent No.: US 7,927,676 B2
(45) Date of Patent: Apr. 19, 2011

(54) PLASMA-TREATED VASCULAR OCCLUSION DEVICES AND METHODS

(75) Inventors: Chunlin Yang, Belle Mead, NJ (US); Yufu Li, Bridgewater, NJ (US); Hiep Do, Hillsborough, NJ (US); Matthew Gounis, Waltham, MA (US); Iksoo Chun, Princeton, NJ (US); Richard Champion Davis, III, Plantation, FL (US); Darren R. Sherman, Ft Lauderdale, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 302 days.

(21) Appl. No.: 11/395,474

(22) Filed: Mar. 31, 2006

(65) Prior Publication Data

US 2007/0239205 A1  Oct. 11, 2007

(51) Int. Cl.
*B65D 39/00* (2006.01)
*B32B 15/08* (2006.01)
*A61D 1/00* (2006.01)

(52) U.S. Cl. .................. 428/36.5; 428/35.8; 606/213
(58) Field of Classification Search ............... 428/34.1; 606/213
See application file for complete search history.

(56) References Cited

U.S. PATENT DOCUMENTS

| | | | |
|---|---|---|---|
| 4,919,659 A * | 4/1990 | Horbett et al. ........... 427/2.25 |
| 5,132,108 A | 7/1992 | Narayanan et al. |
| 5,244,654 A | 9/1993 | Narayanan |
| 5,336,518 A | 8/1994 | Narayanan et al. |
| 5,409,696 A | 4/1995 | Narayanan et al. |
| 5,462,781 A * | 10/1995 | Zukowski ................. 428/36.1 |
| 5,486,357 A | 1/1996 | Narayanan |
| 5,591,140 A | 1/1997 | Narayanan et al. |
| 5,690,671 A | 11/1997 | McGurk et al. |
| 5,980,550 A | 11/1999 | Eder et al. |
| 6,024,754 A | 2/2000 | Engelson |
| 6,033,582 A | 3/2000 | Lee et al. |
| 6,165,198 A | 12/2000 | McGurk et al. |
| 6,187,024 B1 | 2/2001 | Boock et al. |
| 6,280,457 B1 | 8/2001 | Wallace et al. |
| 6,299,627 B1 | 10/2001 | Eder et al. |
| 6,602,261 B2 | 8/2003 | Greene et al. |
| 6,620,194 B2 | 9/2003 | Ding et al. |
| 6,723,108 B1 | 4/2004 | Jones et al. |
| 7,056,550 B2 | 6/2006 | Davila et al. |
| 2001/0044629 A1 * | 11/2001 | Stinson ..................... 606/108 |
| 2002/0087184 A1 * | 7/2002 | Eder et al. .................. 606/191 |

(Continued)

FOREIGN PATENT DOCUMENTS

EP  1 192 957 A2  4/2002

(Continued)

OTHER PUBLICATIONS

European Search Report and Annex dated Sep. 12, 2007, in EP 07 251266.

*Primary Examiner* — Rena L Dye
*Assistant Examiner* — James Yager
(74) *Attorney, Agent, or Firm* — Cook Alex Ltd.

(57) ABSTRACT

Vaso-occlusive devices are provided that have a polymer foam disposed about them. The polymer is treated with a plasma to facilitate thrombogenicity. A method for making and using such devices also is provided. The preferred polymer is a copolymer of a halogenated vinylidene and a halogenated alkene.

3 Claims, 4 Drawing Sheets

U.S. PATENT DOCUMENTS

| | | |
|---|---|---|
| 2002/0094440 A1 | 7/2002 | Llanos et al. |
| 2004/0059370 A1 | 3/2004 | Greene et al. |
| 2004/0142094 A1 | 7/2004 | Narayanan |
| 2004/0225346 A1* | 11/2004 | Mazumder et al. .......... 623/1.13 |
| 2005/0037133 A1 | 2/2005 | Halleriet et al. |
| 2005/0038504 A1 | 2/2005 | Halleriet et al. |
| 2007/0009565 A1 | 1/2007 | Pacetti et al. |

FOREIGN PATENT DOCUMENTS

| | | |
|---|---|---|
| EP | 1 192 957 A3 | 2/2004 |
| WO | WO 99/44538 | 9/1999 |
| WO | WO 00/37971 | 6/2000 |

* cited by examiner

PLASMA-TREATED VASCULAR OCCLUSION DEVICES AND METHODS

FIELD OF THE INVENTION

The present invention is related to vascular occlusion systems that facilitate embolization and thrombus formation within the vascular system of a patient and methods for manufacturing such devices.

BACKGROUND OF THE INVENTION

The deployment of vaso-occlusive devices such as embolic coils in the vasculature of the human body has become a standard procedure for treating endovascular diseases such as aneurysm. These devices are particularly useful in treating areas where traditional surgical procedures are impossible or pose a great risk to the patient, for example, in the treatment of aneurysms in cranial blood vessels. The deployment of vaso-occlusive devices is often accomplished using a delivery catheter. A vaso-occlusive device, such as an embolic coil, is attached to the end of a delivery member which pushes the coil through the catheter and out of the distal end into the delivery site.

In the case of aneurysm, vaso-occlusive devices such as embolic coils act by occluding the flow of blood to a vessel. The reduction of blood flow to the aneurysm reduces the blood pressure in the area of the aneurysm and reduces the risk of a burst aneurysm. Furthermore, the insertion of the vaso-occlusive device may facilitate thrombus formation in or at the site of the aneurysm. For example, the vaso-occlusive device may act as a scaffold upon which thrombus formation is initiated. In the optimal situation, thrombus formation is followed by neointima formation and then fibrosis. As a result, the blood flow within the aneurysm may be permanently occluded and the risk of a burst aneurysm is greatly reduced. However, in a significant number of cases re-canalization occurs, whereby blood flow is re-established. The resumption of blood flow may lead to compaction of the vaso-occlusive device, an increase in the size of the aneurysm and ultimately increase the risk of a burst aneurysm.

Embolic coils have been developed that can assume different shapes to occupy the space of a particular blood vessel. In addition, the coil may have a coating in the form of a foam that increases the volume occupied by the coil and improves the degree of occlusion The thrombogenic properties of a coil may also be increased by disposing a coating material about the coil. U.S. Pat. No. 5,690,671 discloses coating the coil with collagen to increase the thrombogenic response. In this case, however, the presence of collagen can induce a thrombolytic response rather than a thrombogenic response. In U.S. Pat. No. 5,980,550, a coil is described wherein an outer water-soluble material is placed over an inner thrombogenic material. The dissolution of the outer layer in the patient leads to the exposure of the inner layer. However, in this case, there is little control over the rate of dissolution of the outer layer and the thrombogenic material may be exposed before correct insertion of the device or it may not be exposed adequately. These patents and other references listed herein are incorporated hereinto by reference.

Art such as this have problems making them less than satisfactory for a variety of reasons. Therefore, a need remains for a vaso-occlusive device system that addresses such problems and promotes thrombogenicity and prevents re-canalization to a more favorable and consistent extent and with a longer term of success than vaso-occlusive devices and manufacturing methods available heretofore.

SUMMARY OF INVENTION

The present invention provides for vaso-occlusive devices that facilitate thrombus formation and methods for making such vaso-occlusive devices. Generally, a vaso-occlusive device is coated with a polymer that has been exposed to plasma gas. The plasma treatment improves the thrombogenic properties of the vaso-occlusive device.

In various embodiments, the polymer may be in the form of a foam and may be non-absorbable. In a preferred embodiment, the polymer is a porous, non-absorbable foam when present on the coil. Poly (vinylidene fluoride-co-hexafluoropropylene) is a preferred polymer. Preferred ratios of polyvinylidene fluoride to hexafluoropropylene in the copolymer range between about 60:40 and about 95:5. These polymers can be generally referred to as PVDF/HFP.

Typically, the products are made by techniques including radiofrequency plasma generation. Embodiments include using plasmas that are or incorporate air, oxygen, helium, hydrogen, ammonia, hydrogen peroxide, water vapor, and combinations thereof as sources of gas.

A general aspect of the present invention is to provide vaso-occlusive devices that have an activated surface and to methods for providing same.

Another aspect of this invention is to provide devices for aneurysm emobilization improvements in cell compatibility and facilitation of intra-aneurysm emobilization and subsequent neointima formation and intra-aneurysm fibrosis.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein.

DESCRIPTION OF THE PREFERRED EMBODIMENTS

Figure 1:
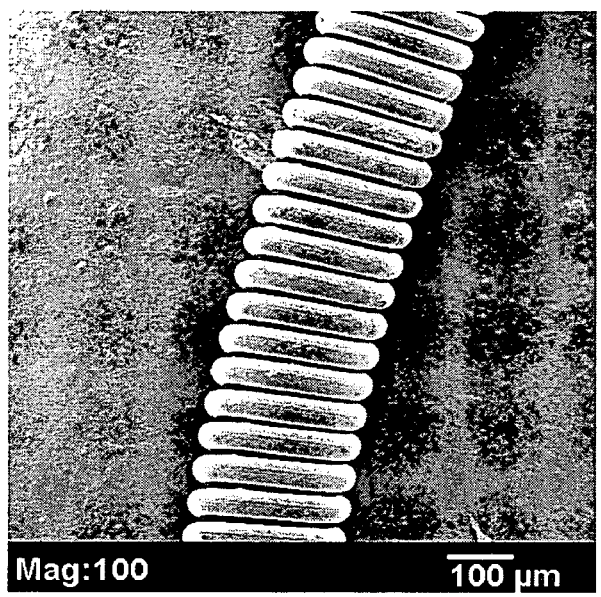
FIG. 1 is a scanning electron micrograph (SEM) of the vaso-occlusive device deployment system of a preferred embodiment of the present invention.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The disclosure provides for devices that facilitate thrombus formation and reduce the chance of recanalization in occluded blood vessels and methods for making such devices. Special application is found for devices that are vaso-occlusive such as embolic coils.

In one embodiment, a vaso-occlusive device in a blood vessel facilitates thrombus formation, ultimately leading to neoinitima and fibrosis. The vaso-occlusive device may act as a scaffold onto which the cells and molecules involved in thrombus formation migrate. This scaffold property is enhanced by the presence of a polymer disposed about the vaso-occlusive device. The vaso-occlusive device with disposed polymer is treated with plasma gas before insertion into the vasculature. The plasma treatment may enhance the ability of cells and molecules to bind to the vaso-occlusive device with disposed polymer, thereby facilitating thrombus formation.

As examples of typical vaso-occlusive devices, it is noted that U.S. Pat. No. 6,723,108 discloses characteristics of various possible different shapes of embolic coils, and this patent and other references identified herein are herein incorporated by reference. A vaso-occlusive device may be in the form of a coil with a lumen, such as a lumen defined by the shape or windings of the coil itself. The coil may also assume higher order shapes that are suitable for occluding blood vessels. The vaso-occlusive device may be delivered using a catheter and a push rod. In cases such as these, the device may assume different shapes when present in the lumen of the catheter or when delivered to the blood vessel. Alternatively, coil stretching and shape changes can be restricted or enhanced by including manipulation or connection features such as incorporating fibres that join two or more points along a coil.

The basic structure of the vaso-occlusive device of the invention can be made of any biocompatible material. Included are metals, alloys and or polymers. The coil material may be radio-opaque. A preferred radio-opaque coil material is platinum. All or part of the coil is coated with a polymer as discussed herein. When the vaso-occlusive device is formed from the polymer itself that is treated with plasma gas as discussed herein, the polymer may be reinforced to provide added shape and/or strength characteristics. For example, reinforcement can be accomplished with fibrous or filamentous material.

When attachment is needed, the polymer material may be secured to the vaso-occlusive device using a variety of approaches. Such include thermal, adhesive and mechanical approaches including heat bonding of components together, joining with a medical-grade adhesive and wraps, clips, inter-engaging members and the like.

In another embodiment, the plasma treatment of the polymer enhances the ability of platelets to bind to the vaso-occlusive device. Although not wishing to be bound by any specific or detailed theory, the polymer disposed about the vaso-occlusive device may undergo chemical changes as a result of the plasma treatment that improve the binding of platelets to the vaso-occlusive device and/or its polymer. Such possible changes in the surface chemical properties of the polymer are suggested by testing that shows decreases in the water contact angles of the polymer after plasma treatment, indicating improved wetting properties of the polymer. Such changes are also suggested by changes in the elemental composition of the surface of the polymer.

In accordance with accepted practices, the plasma gas is generated by radiowaves as generally known in the art. For example, the U.S. Federal Communication Commission mandates the frequency of the radiowaves to be at 13.56 MHz.

The gas used to generate the plasma may be oxygen, air, inert gases such as helium, and/or argon, water vapor, hydrogen, ammonia, hydrogen peroxide or combinations thereof. Preferred gases include hydrogen, helium, and blends of hydrogen and helium.

Plasma gas may be generated by a radiowaves having a power of about 10 to about 1000 watts, preferably about 100 to about 400 watts. The polymer may be exposed to the plasma gas for a period of about 1 second to about 60 minutes, with a preferred exposure time of about 1 minute to about 10 minutes. Plasma treatment may be performed at atmospheric pressure. Preferably, the treatment is performed at about 1 millitorr to about 1 atmosphere, more preferably about 50 to about 200 millitorr.

In one embodiment, the polymer is biocompatible but is non-absorbable. A non-absorbable polymer will not be affected by biological processes and will therefore provide a longer-lasting scaffold upon which thrombus formation can occur when this is the desired effect. Such effect can be preferred for these types of devices.

In different embodiments, the polymer can form foams as discussed herein. These foams can be either porous, non-porous, or combinations thereof. A foam is advantageous in that the inserted vaso-occlusive device can occupy a greater volume of the blood vessel and therefore increase the occlusive properties of the vaso-occlusive device. A porous foam is advantageous in that it provides a larger surface area than does a non-porous surface or a surface with less foam formation. Such larger surface area is advantageous for enhancing the binding of the cells and molecules involved in thrombus formation. In a preferred embodiment, these cells and molecules are better able to enter the lumen of the vaso-occlusive device due to the degree of porosity of the foam.

Methods for manufacturing a foam of a polymer are known per se in the art. They include freeze drying or lyophilization, supercritical solvent foaming, extrusion or mold foaming with fugitives or casting with an extractable material. Foam formation by lyophilization typically is particularly useful because it is a simple process that does not require high temperatures and allows the control of the degree of porosity. In lyophilization, in accordance with generally know practices, a solution of the polymer is frozen such that the polymer and the solvent separate into different phases. The solvent is removed by lyophilization leaving a porous polymer.

Polymers which can be used in the invention include polyamides, polyurethanes, and silicones. Preferred polymers are copolymers, such as those that are a copolymer of a halogenated vinylidene and a halogenated alkene that has a short carbon chain length typically between about C-1 and about C-12. Preferred carbon chain lengths are between about C-2 and C-6, and preferred halogenation is with fluorine components.

In a particularly preferred embodiment, the polymer is poly(vinylidene fluoride-co-hexafluropropylene), which is referred to herein at times as PVDF/HFP. The weight ratio of halogenated vinylidene (PVDF in the preferred embodiment) to halogenated alkene (HFP in the preferred embodiment) typically is between about 60:40 and about 95:5, preferably between about 70:30 and about 90:10, more preferably between about 80:20 and about 90:10. An especially preferred ratio of PVDF to HFP in the preferred copolymer is 85:15.

The exposure of the polymer to plasma gas results in the reduction in the water contact angle (WCA) of the polymer. After exposure to plasma gas, the WCA of the polymer is in the range of from about 35 to about 85 degrees. The decrease in WCA indicates that the polymer has become more hydrophilic, suggesting changes in the surface properties of the polymer.

Examples are now provided in order to illustrate the concepts of the invention with a certain degree of specificity.

Example 1

An embolic coil is prepared with a non-absorbable polymer as a foam coating. To prepare a 2% weight/weight solution of 85/15 poly(vinylidene fluoride-co-hexafluoropropylene) (available, for example, from Aldrich, St. Louis, Mo., USA), 1.04 grams of this copolymer was added to 49.34 grams of 1,4-dioxane (available from Fisher Scientific, Raritan, N.J., USA). The mixture was stirred for 24 hours in a 60° C. water bath set on a controlled-temperature heating plate. The copolymer solution was filtered through an extra-coarse thimble to remove undissolved solids. A 1% weight/weight copolymer solution was prepared by adding 10 grams of 1,4-dioxane to 10 grams of the 2% solution.

A 15 cm embolic coil (such as the coil shown in FIG. 1) was inserted into a section of PTFE (polytetrafluoroethylene) tubing (0.015 inch inner diameter, available from Zeus Industrial Products, Orangeburg, S.C., USA) that was 2 cm longer than the coil. The tubing served as mold when the copolymer solution was added. The 1% weight/weight copolymer solution was added to the mold using a glass syringe with a 30 gauge needle. The mold with coil and polymer solution was sonicated for approximately 5 minutes to ensure that the solution reached the lumen of the coil. The sonication was within a sonication bath provided by a sonication unit (Model 3210R-DTH of Branson, Danbury Conn., USA). Bubbles generated by sonication were flushed with fresh polymer solution.

The mold then was frozen in liquid nitrogen for five minutes and placed on a shelf of a freeze dryer maintained at −17° C. The mold was subjected to the following cycles of freeze-drying to remove solvent that are set out in Table 1. After completion of the lyophilization process, the coil with disposed polymer as a foam coating was removed from the mold.

TABLE 1

| Temp ° C. | Pressure (mmTorr) | Hold Time (min) |
|---|---|---|
| −17 | Ambient | 15 |
| −17 | Ambient | 60 |
| −5 | 20 | 1200 |
| 5 | 20 | 180 |
| 20 | 20 | 120 |

Example 2

Figure 2:
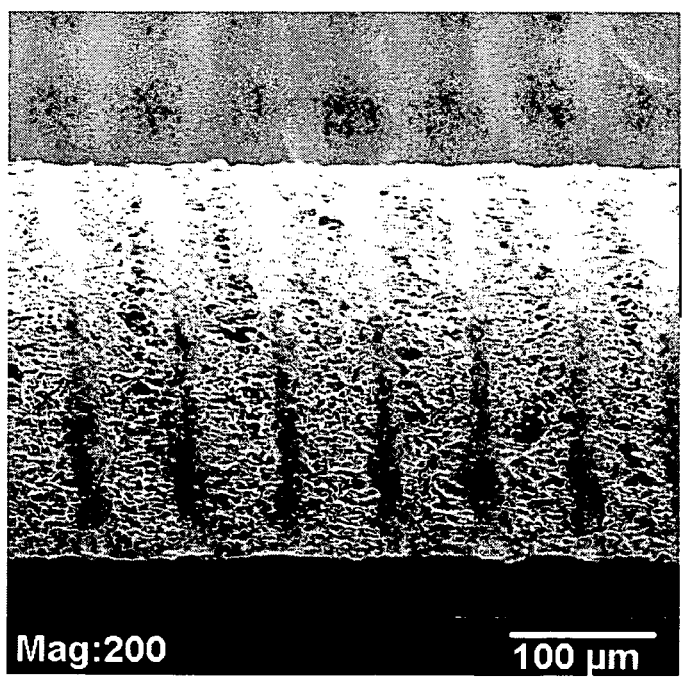
FIG. 2 is a scanning electron micrograph (SEM) of a PVDF/HFP foamed vaso-occlusive device.

A series of foam-coated PVDF/HFP embolic coils made in accordance with Example 1 were examined using an SEM (JEOL JSM-5900LV) and evaluated. For each coil, the middle section and end sections were examined. FIG. 2 is a scanning electron micrograph (SEM) of a foam coil as prepared in this Example. As evident from FIG. 2, PVDF/HFP foam with interconnected pores was seen both in the coil lumen and outside of the coil. Some pores extended from the outer surface of the foam into the lumen of the coil.

Example 3

The effect of plasma treatment on water contact angles of PVDF/HFP polymer was studied using air as a gas. PVDF/HFP copolymer made in accordance with Example 1 was compressed into an approximately 1 mm film by applying a 20,000 pounds (approximately 9000 kg) force at 225° C. using a 30 ton Carver compressor (Model 2696, Carver Inc., Wabash, Ind., 46992). The films were washed sequentially with soap water, isopropyl alcohol, and chloroform.

The films were treated with plasma generated with a chromium type plasma instrument (Model HV2010, Tantec-EST, Lunderskov, Denmark). The films were treated in air at atmospheric pressure under 17 kV and 47 watts for either 2 minutes or 10 minutes.

Figure 3:
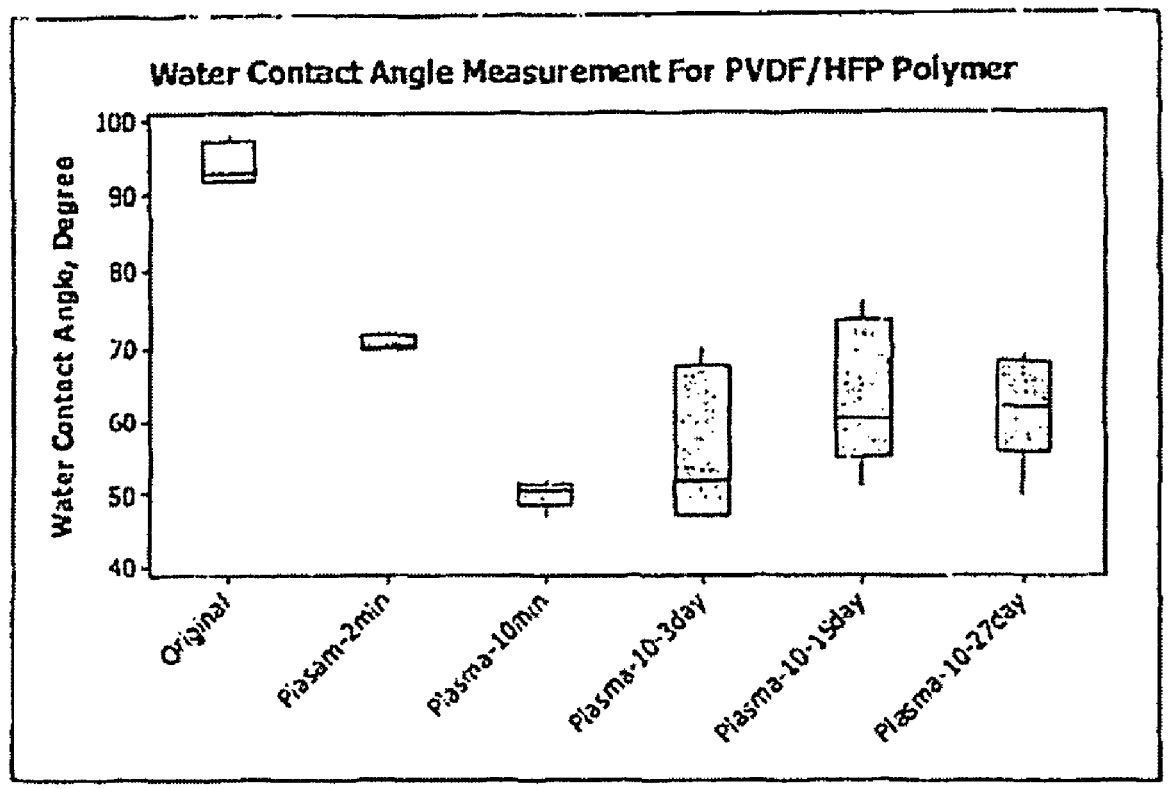
FIG. 3 is a graph showing the effect of plasma treatment on the water contact angles of PVDF/HFP polymer using air at atmospheric pressure as a gas in accordance with Example 3.

Water contact angles (WCA) were determined using a NRL contact angle gonometer (Model 100-00 115 from Rame Hart Inc., Mountain Lakes, N.J., USA). WCA values were determined either immediately after plasma treatment or after periods of 3, 15 or 27 days. As shown in FIG. 3, plasma treatment decreases the water contact angle of the polymer. In FIG. 3, each bar represents the range of WCA observed and the horizontal line across each bar indicates the median value for each sample. Untreated films have WCA values of greater than 90 degrees, indicating poor hydrophilicity of the untreated polymer surface. All polymer samples treated with plasma have a WCA of less than 90 degrees, indicating a better hydrophilic surface in plasma treated samples.

Example 4

The effect of plasma treatment on water contact angles of PVDF/HFP polymer using helium as a plasma gas was evaluated. PVDF/HFP copolymer used to make foam in accordance with Example 1 was compressed into films with approximately 1-mm thickness by applying a 20,000-pound (~9000 kg) force at 225° C. using a 30-ton (~13600 kg) Carver compressor. The films were washed sequentially with soap water, isopropyl alcohol, and chloroform.

The films were clipped individually using small paper clips, then placed in the chamber of a plasma reactor (Model: PS-350, available from AST Products, Inc., Billerica, Mass. 01821). The chamber was evacuated then purged by helium gas. Sequentially, the helium pressure in the chamber was lowered to 150 mmTorr while retaining the helium gas flow rate at 100 sccm. The plasma was generated by the application of 13.56 MHz and 300 watts for 10 minutes. Compressed air was introduced into the chamber at 1000 sccm flow rate, under 2000 mmTorr for 30 minutes as a post treatment step.

Figure 4:
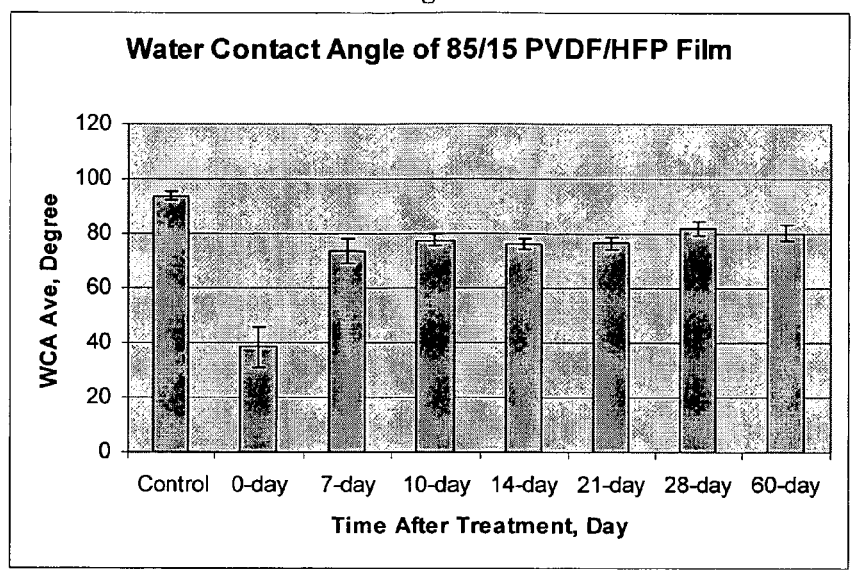
FIG. 4 is a graph showing the effect of plasma treatment on the water contact angles of PVDF/HFP polymer using helium as a gas in accordance with Example 4.
Figure 5:
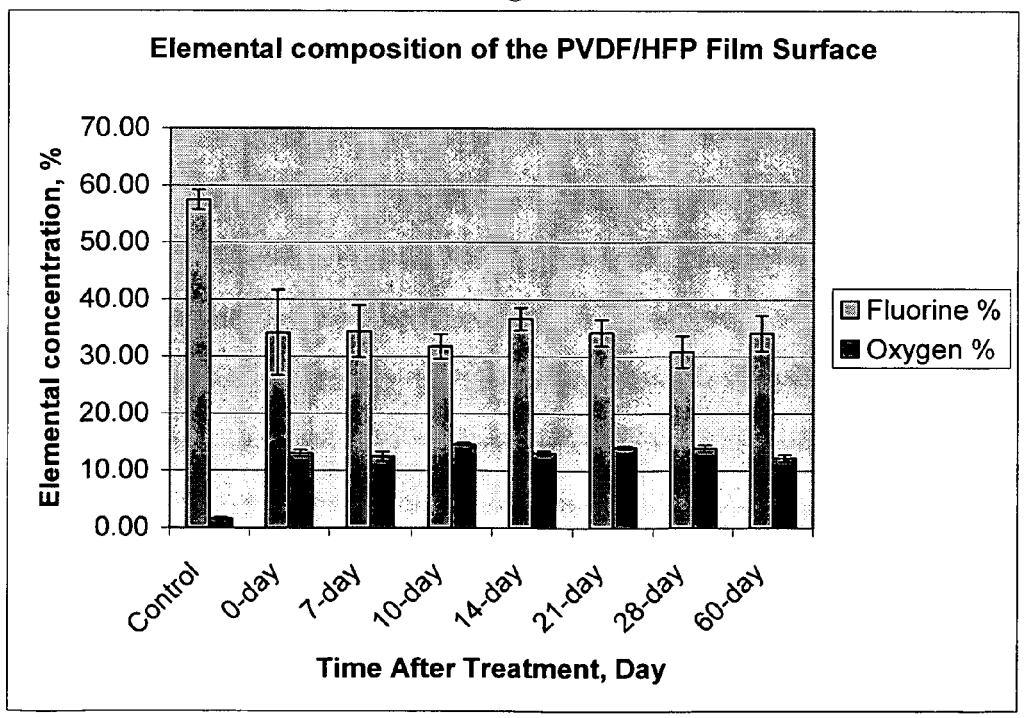
FIG. 5 is a graph showing the elemental composition of the film surfaces of PVDF/HFP polymer treated with helium plasma gas in accordance with Example 4.

The water contact angles (WCA) were determined using a surface analysis system (Model: VCA Optima XE, available from AST Products, Inc.). The elemental compositions were measured using XPS (X-ray photoelectron spectroscopy; Model: Physical Electronics 5700Lsci, East Evens, East Windsor, N.J.). The WCA and elemental compositions were measured at the time points of 0, 7, 10, 14, 21, 28, 60 days after the plasma treatment along with the untreated samples as the controlled ones as shown in FIG. 4 and FIG. 5, respectively. In FIG. 4 and FIG. 5, each bar represents the average of the measurements observed and the error bars indicate the standard deviations. Plasma treatment decreases the water contact angle and fluorine concentration and increases oxygen concentration of the polymer. Therefore, this treatment produces more hydrophilic surfaces which improve the adhesion properties of the polymer surfaces.

Example 5

Vaso-occlusive devices are plasma treated as follows. PVDF/HFP foamed vaso-occlusive devices made in accordance with Example 1 were loosely laid on a Teflon rack which was placed in the chamber of a plasma instrument (Model PDC-002, Harrick Scientific Instruments, Ossining, N.Y. USA). The chamber pressure was lowered to 150 mmTorr. The plasma was applied by the application of 13.56 mHz, 750 volts and 29 watts for 10 minutes.

Example 6

The effect of plasma treatment on the adhesion of platelets to the PVDF/HFP vaso-occlusive devices was tested. For these experiments, plasma-treated coils were prepared in accordance with Example 5. Blood was obtained from Holstein cows and anti-coagulated with heparin (1.5-2 U/ml concentration). To label platelets, 500 of autologous blood was collected in acid citrate dextrose (ACD) and centrifuged at 350G to remove red cells. Platelets were sedimented by centrifugation at 1000 G for 15 minutes at 22° C., and the plasma fraction of the blood was decanted. The platelets were resuspended in 5 milliliters of ACD-saline, and 100 µCi of $^{111}$Indium Oxine was added and the mixture incubated at 37° C. for 20 minutes. The $^{111}$In labeled platelets were added back to whole blood prior to the commencement of the experiment.

To test the adhesive properties of the plasma-treated vaso-occlusive devices, the blood from a single animal was divided into separate 1 liter blood reservoirs. Vaso-occlusive devices that had been subjected to one of the treatments in Table 2 below were deployed in polyvinyl chloride (PVC) conduits (3.2 millimeter diameter), and the conduits were placed in one of the reservoirs. The control embolic coils 1 and 2 did not have polymer disposed about them. Control 1 is a straight platinum wire manufactured by Cordis. Control 2 is a commercially available coiled and twisted platinum wire braided with polymer fiber.

TABLE 2

| Configuration ID | Description |
| --- | --- |
| Control 1 | Straight platinum |
| Control 2 | Coiled platinum |
| PVDF100 | 1% 85/15 PVDF/HFP |
| PVDF075 | 0.75% 85/15 PVDF/HFP |
| 100P02 | 1% 85/15 PVDF/HFP, 2 minutes plasma treatment |
| 100P10 | 1% 85/15 PVDF/HFP, 10 minutes plasma treatment |
| 075P02 | 0.75% 85/15 PVDF/HFP, 2 minutes plasma treatment |
| 075P10 | 0.75% 85/15 PVDF/HFP, 10 minutes plasma treatment |

Figure 6:
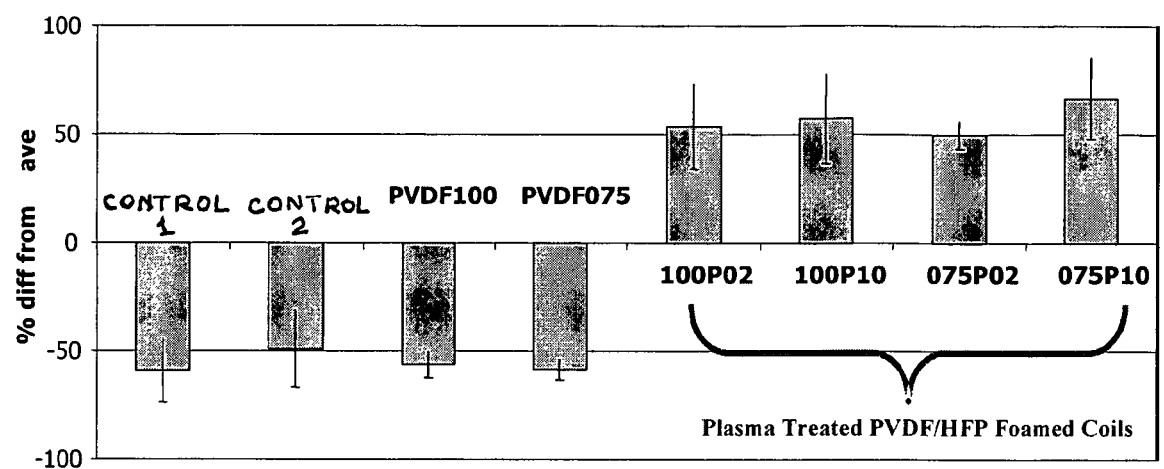
FIG. 6 is a graph showing the effect of plasma treatment of a vaso-occlusive device on platelet adhesion.

A roller pump was used to create blood flow at 65 ml/min and the temperature was maintained at 37° C. Blood flow was monitored continuously and non-invasively with an ultrasonic flow probe. After 45 minutes, the devices were retrieved and platelet adhesion to the vaso-occlusive devices was quantified by measuring the radioactivity associated with the vaso-occlusive device using a gamma counter (Manaxi 5000, available from Packard, Meriden, Conn., USA). Higher radiation indicates more platelets bound to the surface of the coil. An average value of platelet binding was calculated by dividing the sum of all of the radioactivity bound by all coils tested by the number of coils tested. As shown in FIG. 6, the difference of each tested coil from the calculated average was plotted for each coil tested. Those vaso-occlusive devices that had been treated with plasma had significantly more bound platelets when compared to the controls and the polymer coated/untreated coils or coils that did not have polymer disposed about them.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A coated vaso-occlusive product comprising:
a vaso-occlusive device that is an embolic coil;
a polymer disposed about said vaso-occlusive device, the polymer being poly(vinylidene fluoride-co-hexafluoropropylene), a copolymer of vinylidene fluoride and hexafluoropropylene, and the ratio of vinylidene fluoride to hexafluoropropylene in the copolymer is 85:15;
the polymer is in the form of an open cell foam having voids between polymer domains, the polymer foam having been exposed to helium plasma gas at between about 50 and 200 millitorr; and
said polymer foam has a surface flourine composition of less than about 40% and has a surface oxygen composition of at least about 10%, while said polymer foam has a water contact angle of said polymer that has been decreased due to its having been exposed to helium plasma gas, the decreased water contact angle of said polymer being from about 35 to about 85 degrees.

2. The product of claim 1, wherein said vaso-occlusive device is made from a material selected from platinum, nitinol, radio-opaque materials, and combinations thereof.

3. The product of claim 1 wherein said decreased water contact angle of said polymer persists for at least 60 days.

* * * * *